United States Patent [19]

Meyer et al.

[11] Patent Number: 5,268,270
[45] Date of Patent: Dec. 7, 1993

[54] PROCESS FOR PRODUCING PROTEINS USING GRAM NEGATIVE HOST CELLS

[75] Inventors: Thomas F. Meyer; Roman Halter; Johannes Pohlner, all of Tübingen, Fed. Rep. of Germany

[73] Assignee: Max-Planck-Gesellschaft zur Förderung der Wissenschaften e.V., Göttingen, Fed. Rep. of Germany

[21] Appl. No.: 171,872

[22] PCT Filed: Jul. 1, 1987

[86] PCT No.: PCT/EP87/00356

§ 371 Date: Feb. 29, 1988

§ 102(e) Date: Feb. 29, 1988

[87] PCT Pub. No.: WO88/00238

PCT Pub. Date: Jan. 14, 1988

[30] Foreign Application Priority Data

Jul. 2, 1986 [DE] Fed. Rep. of Germany ....... 3622221

[51] Int. Cl.$^5$ .................. C12P 21/02; C12P 19/34; C12N 15/00; C12N 7/00; C12N 1/21; C07H 15/12; C07K 3/00

[52] U.S. Cl. .................. 435/69.1; 435/172.3; 435/235.1; 435/320.1; 435/252.3; 435/252.38; 536/23.4; 536/23.2; 536/23.7; 530/350; 935/10; 935/19; 935/29; 935/48; 935/56; 935/61; 935/43

[58] Field of Search ............ 435/68, 69.1, 70, 320, 435/172.1, 252.33; 536/27; 530/350; 335/19, 29, 48, 56, 60, 73, 81

[56] References Cited

U.S. PATENT DOCUMENTS

4,338,397  7/1982  Gilbert et al. .................... 435/68

OTHER PUBLICATIONS

Kooeny et al. Proc. Natl. Acad. Sci. USA vol. 79 pp. 7881–7885 (1985).
Zemel-Dreasen Gine vol. 27 pp. 315–322 (1984).
Halter et al. EMBO vol. 3 pp. 1595–1601 (1984).
Pohlner et al. Nature vol. 335 pp. 458–462 (1987).

*Primary Examiner*—Joan Ellis
*Attorney, Agent, or Firm*—Felfe & Lynch

[57] ABSTRACT

For the gene-technological production of proteins, a vector is introduced into gram-negative host cells which contains at least one gene coding translated. For the extracellular obtaining of the proteins its coding gene is so inserted into a vector which contains the IgA-protease precursor gene from micro-organisms of the genus Neisseria that the coding gene is positioned within the sequence of the IgA-protease precursor gene. A plasmid especially suitable for this purpose is the plasmid pIP100 contained in *E. coli* DSM 3775.

9 Claims, 19 Drawing Sheets

FIG. 1A

```
GCAATAAAACACCAAAATGAATGAGTTTACACAAAAAAATACTCAACACCACCCAACCGGCGTAAAATGCAAAAC                75
ATTATCGCTATTAAAACGGTAAAACCTTATGAAAGCCAAACGTTTAAAATTAACGCCATATCCTTATCCATCTT                150
                   M  K  A  K  R  F  K  I  N  A  I  S  L  S  I  F
TCTTGCCTATGCCCTTACGCCATACTCAGAAGCGGCCATTGGTGAGAGACGATGTCGATTATCAAATATTCCGTGA                225
 L  A  Y  A  L  T  P  Y  S  E  A  A  L  V  R  D  D  V  D  Y  Q  I  F  R  D
CTTTGCAGAAAACAAAGGCAAATTTTTGTCGGCGCAACCGATTTATCAGTGAAAAACAAACGAGGTCAAAACAT                300
 F  A  E  N  K  G  K  F  F  V  G  A  T  D  L  S  V  K  N  K  R  G  Q  N  I
CGGCAACGCCATTATCCAACGTACCGATGATTGATTTTAGCGTTGCAGATGTCAACAAACGCATAGCAACGGTAGT                375
 G  N  A  L  S  N  V  P  M  I  D  F  S  V  A  D  V  N  K  R  I  A  T  V  V
CGATCCCCAATATGCCGTCAGCGTCAAACACGCCAAAGCAGAGAAGTCCATACTTTTTATTACGGCCAATACAACGG                450
 D  P  Q  Y  A  V  S  V  K  H  A  K  A  E  V  H  T  F  Y  Y  G  Q  Y  N  G
TCATAATGATGTAGCCGACAAAGAAAATGAATACCGCGTTGTCGAACAAAATAACTATGAACCCCATAAAGCTTG                525
 H  N  D  V  A  D  K  E  N  E  Y  R  V  V  E  Q  N  N  Y  E  P  H  K  A  W
GGGTGCCAGCAATTTAGGCCGCCTCGAAGATTATAATATGGCGCGTTTTAATAAGTTTGTAACCGAAGTGCACC                600
 G  A  S  N  L  G  R  L  E  D  Y  N  M  A  R  F  N  K  F  V  T  E  V  A  P
GATTGCACCAACTGATCGCCGGGCGATTGATAACCTACAAAGATAAAAACCGTTTTCCTCTTTTGTCAGAAT                675
 I  A  P  T  D  A  G  G  L  D  T  Y  K  D  K  N  R  F  S  S  F  V  R  I
CGGTGCGGGCAGCAATTAGTTTATGAAAAGGGGTTTATCATCAAGAAGGAAATGAAAAGGCTACGATTTGCG                750
 G  A  G  R  Q  L  V  Y  E  K  G  V  Y  H  Q  E  G  N  E  K  G  Y  D  L  R
CGATCTTTCACAAGCCTATCGTATGCCATTGCAGTGTACGCCTTATAAAGATATTGACCAAACAATGAA                825
 D  L  S  Q  A  Y  R  Y  A  I  A  G  T  P  Y  K  D  I  N  I  D  Q  T  M  N
TACCGAAGGTTTGATCGGCTTTGGTAATCATAATAAACAGTATTCGGCAGAAGAACTTAAACAAGCACTTTCGCA                900
 T  E  G  L  I  G  F  G  N  H  N  K  Q  Y  S  A  E  E  L  K  Q  A  L  S  Q
AGATGCGTTAACAAATTACGGCGTGTTGGGCGATAGCGGCTCTCCACTATTGCTTTTGACAAACAAAAAATCA                975
 D  A  L  T  N  Y  G  V  L  G  D  S  G  S  P  L  F  A  F  D  K  Q  K  N  Q
ATGGGTCTTTTTGGAACTTACGATTATTGGGCAGGTTACGGAGAAAAATCATGGCAAGAATGAATATCTATAA                1050
 W  V  F  L  G  T  Y  D  Y  W  A  G  Y  G  K  K  S  W  Q  E  W  N  I  Y  K
AAAAGAATTTGCAGATAAAATCAAACAGCATGATAATGCGGGTAAGGCTTGCCAACATGGAGAACATCATTGGAA                1125
 K  E  F  A  D  K  I  K  Q  H  D  N  A  G  T  V  K  G  N  G  E  H  H  W  K
AACCACGGGTACAAACAGCCATATCGTTCGACACCGGTAAGGCTTGCCAACATGGAGAACATCATTGGAA                1200
 T  T  G  T  N  S  H  I  G  S  T  A  V  R  L  A  N  E  G  D  A  N  N  G
ACAAAATGTTACCTTTGAAGACAACGGCACTTTGGTATTGAATCAAAACATCAACCAAGGCGCGGGCGCCCTGTT                1275
 Q  N  V  T  F  E  D  N  G  T  L  V  L  N  Q  N  I  N  Q  G  A  G  G  L  F
```

FIG. 1B

```
TTTCAAAGGCGATTACACAGTCAAAGGCGCAAATAATGACATCACTTGGTTAGGTGCGGGGATTGATGTTGCCGA    1350
  F  K  G  D  Y  T  V  K  G  A  N  N  D  I  T  W  L  G  A  G  I  D  V  A  D
CGGCAAAAAGTCGTTTGGCAAGTCAAAATCGGACAGATTGGCAAAATCGGCAAAGGCACTTTGGA              1425
  G  K  K  V  V  W  Q  V  K  N  P  N  G  D  R  L  A  K  I  G  K  G  T  L  E
AATAAACGGCACAGGCGTTAACCAAGGCAATTAAAGGTCGGCGACGTTATTCTGAATCAAAAGCCGA            1500
  I  N  G  T  G  V  N  Q  G  L  K  V  G  D  G  T  V  I  L  N  Q  K  A  D
TGCCGACAAAAAGTTCAGCTTTCTCCCAAGTCGGCATTGTCAGCGGACGCGGTACATTGTATTAAATAGTTC       1575
  A  D  K  K  V  Q  A  F  S  Q  V  G  I  V  S  G  R  G  T  L  V  L  N  S
AAATCAGATTAATCCCGATAACCTATATTTCGGTTTCCGTGGCCGTCTTGATGCCAATGCAATGACTTGAC        1650
  N  Q  I  N  P  D  N  L  Y  F  G  F  R  G  G  R  L  D  A  N  G  N  D  L  T
TTTGAACACATCCGCAACGTGGATGAAGGCGCGCATTGTCAACACAGACCACGCCTCCACAATCAC             1725
  F  E  H  I  R  N  V  D  E  G  A  R  I  V  N  H  N  T  D  H  A  S  T  I  T
ACTAACGGGTAAATCTTAATTACCAATCCGAACAGCCTTTCGGTACATAGCAAAGATCTTTATTACAAAACTATCGTTA 1800
  L  T  G  K  S  L  I  T  N  P  N  S  L  S  V  H  S  I  Q  N  D  Y  D  E  D
TGATTATAGTTATTATTACGGACCAAGGCGACCATCCCACAAGGCAAAGATCTTTATTACAAAGATCTTTATTACGTTA 1875
  D  Y  S  Y  Y  Y  R  P  R  P  I  P  Q  G  K  D  L  Y  K  N  Y  R  Y
TTACGCCCTAAAATCCGGCGGCCAGGCTGAACGCACCGAGAACGTGTAGCAGAAATAACGACTGGAT            1950
  Y  A  L  K  S  G  G  R  L  N  A  P  M  P  E  N  G  V  A  E  N  N  D  W  I
CTTTATGGGATATACGCAGGAGGAGGCCAGGAGAAAACGGATGAACACAAAACAATCGGCGTATTGGCGATTT      2025
  F  M  G  Y  T  Q  E  E  A  R  K  N  A  M  N  H  K  N  R  R  I  G  D  F
TGGCGGTTTCTTTGACGAAGAAAACGGAAAAGGACATAACGGCCATTAAACCTTAATTTCAATGGCAAAAGCGC     2100
  G  G  F  F  D  E  E  N  G  K  G  H  N  G  A  L  N  L  N  F  N  G  K  S  A
GCAAAACCGTCTTCTTGTTAACAGGCGCGCCAATTAAACGGAAAATAAGCGTAACTCAAGGCAATGTCTTGTT      2175
  Q  N  R  F  L  L  T  G  G  A  N  L  N  G  K  I  S  V  T  Q  G  N  V  L  L
ATCAGTCGTCCAACACCACACGGCAAGAGATTTTGTGAACAAATCTTCAGCCCGAAAGACGCACATTTCTCCAA     2250
  S  G  R  P  T  P  H  A  R  D  F  V  N  K  S  S  A  R  K  D  A  H  F  S  K
AAACAATGAAGTCGTATTTGAAGACGACTGGATAAACCGCACATTCAAAGCCCAGAAATTGCGGTTAACCAATC     2325
  N  N  E  V  F  E  D  D  W  I  N  R  T  F  K  A  A  E  I  A  V  N  Q  S
CGCATCATTCTTCCGGAAGAAATGTATCCGACATCACCGCCAACATCACCGACAACGCCAAAGTAAA            2400
  A  S  F  S  S  G  R  N  V  S  D  I  T  A  N  I  T  A  T  D  N  A  K  V  N
TTTGGGTTACAAAACGGCGATGAGTTTGCGTGCCGCTCGGACTATACCGGTTACGTTACCTGCAACACAGGCAA     2475
  L  G  Y  K  N  G  D  E  V  C  V  R  S  D  Y  T  G  Y  V  T  C  N  T  G  N
CTTATCCGATAAGGCTTTAAACAGCTTTGATGCGACACGGATTAACGGATTGAATTGAATTGAATCAGAATGCGGC   2550
  L  S  D  K  A  L  N  S  F  D  A  T  R  I  R  N  G  N  V  N  L  N  Q  N  A  A
```

FIG. 1C

```
ATTGGTCTTGGGCAAGGCTGCATTATGGGGAAAATTCAAGGACAAGGAAACAGCCGTGTCAGCCTAAACCAACA    2625
 L  V  L  G  K  A  A  L  W  G  K  I  Q  G  Q  G  N  S  R  V  S  L  N  Q  H
TAGCAAATGGCCATTTGACCGGCGACACCAAGTACACAACATCTGTCATTGGCGATAGCCATATTCATTTGAACAA    2700
 S  K  W  H  L  T  G  D  S  Q  V  H  N  L  S  L  A  D  S  H  I  H  L  N  N
CGCTTCCGATGCGCAAAGTGCAAATAAATACCACACGATCAAATCAATCATTATCCGTAACGGCATTTCA        2775
 A  S  D  A  Q  S  A  N  K  Y  H  T  I  K  I  N  H  L  S  G  N  G  H  F  H
TTATCTGACGGACTTGGCGAAAAATCTTGGGGATAAAGTGCTTGTGAAGAATCCGGCCATTATCAGCT          2850
 Y  L  T  D  L  A  K  N  L  G  D  K  V  L  V  K  E  S  A  S  G  H  Y  Q  L
CCATGTTCAAAATAAACAGGCGAACCTAATCAGGAAGGGCTGGATCTCTTTGATGCATCATCCGTACAAGACCG    2925
 H  V  Q  N  K  T  G  E  P  N  Q  E  G  L  D  L  F  D  A  S  S  V  Q  D  R
CTCCCGCCTTTTGTTCCTTGCAAATCATTAGTCGATTTAGGCGATTGCGTTATACAATCAAAACAGAAAA        3000
 S  R  L  F  V  S  L  A  N  H  Y  V  D  L  G  A  L  R  Y  T  I  K  T  E  N
CGGTATTACCCGGTTGTACAAGCACACAAAAGGCAACACAAACGACGGTGCACAAATTGCCAAGCCTCAAGCCGT  3075
 G  I  T  R  L  Y  N  P  Y  A  G  N  G  R  P  V  K  P  A  P  S  P  A  A  N
CACGGCCTTCTCAAGCACAAATCAAGCCGCAGGCCAAATCAAGCCGCCAACAACAAAGCGAGCAAGTGAAGCGTCA  3150
 T  A  S  Q  A  Q  K  A  T  Q  T  D  G  A  Q  I  A  K  P  Q  N  I  V  A
ACCGCCTAGCCCGCAGGCCAAATCAAGCCGCAGAAGCCCTCCGCCAACAACAAAGCGAGCAAGTGAAGCGTCA    3225
 P  P  S  P  Q  A  N  Q  A  E  E  A  L  R  Q  Q  A  K  A  E  Q  V  K  R  Q
GCAAGCAGCAGAAGCAGAAAAGTTGCACGTGCAGAGTTAGCCGCCAAAAGACCAGAAGCCAAAGAGCCAGAGA    3300
 Q  A  E  A  E  K  V  A  R  Q  K  D  E  E  A  K  R  K  A  A  E  I  A  R
TCAGCAGGAAGAAAGCACGAAAAGCAGAGAGGCAAGTCATCAAGCTAATGCCAAACCAAAACGTCGTAGACGTCGGGCTAT  3375
 Q  Q  E  E  A  R  K  A  A  E  L  A  A  K  Q  K  A  E  A  E  R  K  A  R  E
GTTGGCAAGACAAAAGCAGAAGAGGCAAGTCATCAAGCTAATGCCAAACCAAAACGTCGTAGACGTCGGGCTAT    3450
 Q  Q  E  E  A  R  K  A  A  E  L  A  A  K  Q  K  A  E  A  E  R  K  A  R  E
ATTACCTAGACCTCCTGCCCAGTATTTCATTGATGATTATGATGCAAAAGACAATAGTGAATCATCAATAGG     3525
 L  A  R  Q  K  A  E  E  A  S  H  Q  A  N  A  K  P  K  R  R  R  R  A  I
TAATTTAGCTCGTGTAATACCTAGAATGGGAAGGGAGTTAATTAATGATTATGAAGAAATCCCCTTGGAGGAGTT  3600
 L  P  R  P  P  A  P  V  F  S  L  D  D  Y  D  A  K  D  N  S  E  S  S  I  G
GGAAGATGAAGCGGAAGAAGAACGTCGCCAAGCAACGTCGAATCGTTCCACTCCAAAAGTCGTAACCGTAGAGCTATATC 3675
 N  L  A  R  V  I  P  R  M  G  R  E  L  I  N  D  Y  E  E  I  P  L  E  E  L
ATCGGAACCATCATCGATGAAGATGCATCTGAATCGTTCCACATCAGACAAACACCCTCAAGATAATACGGA    3750
 E  D  E  A  E  E  E  R  R  Q  A  T  Q  F  H  S  K  S  R  N  R  R  A  I  S
ACTTCATGAAAAAGTTGAGACGCGGGGTTTACAACCAAGACGCCGCCAGCCCGAACCAACGCCGCGAAGC       3825
 S  E  P  S  S  D  E  D  A  S  E  S  V  S  T  S  D  K  H  P  Q  D  N  T  E
 L  H  E  K  V  E  T  A  G  L  Q  P  R  A  A  Q  P  R  T  Q  A  A  A  Q  A
```

FIG. 1D

```
CGATGCAGTCAGCACCAATACTAACTCGGCTTTATCTGACGCAATGGCAAGCACGCAATCTATCTTGTTGATAC    3900
 D   A   V   S   T   N   T   N   S   A   L   S   D   A   M   A   S   T   Q   S   I   L   L   D   T
AGGTGCTTACTTAACACGGCACATTGCACAAAATCACGCGCTGATGCCGAAAACAGTGTTTGGATGTCAAA        3975
 G   A   Y   L   T   R   H   I   A   Q   K   S   R   A   D   A   E   K   N   S   V   W   M   S   N
CACCGGTTATGCCGTGATTATGCTTCCGCACAATATCGCCGTTTAGTTCGAAACGCACGCAAACACAAATCGG      4050
 T   G   Y   G   R   D   Y   A   S   A   Q   Y   R   R   F   S   S   K   R   T   Q   T   Q   I   G
CATTGACCGCAGCTTGTCCGAAAATATGCAGATAGGCGGAGTATTGACTTACTCTGACAGTCAGCATACTTTTGA    4125
 I   D   R   S   L   S   E   N   M   Q   I   G   G   V   L   T   Y   S   D   S   Q   H   T   F   D
TCAGGCGGGGCAAAAATACTTTTGTGCAAGCCAACCTTTATGGTAAGTATTATTTAAATGATGCTTGGTATGT      4200
 Q   A   G   G   K   N   T   F   V   Q   A   N   L   Y   G   K   Y   Y   L   N   D   A   W   Y   V
GGCCGGCGATATGTGCGGGCAGCTTGAGAAGCCGTGTCGAAATCAATCAATTCGAGATTGTCCCTAGTGCCGGGTATCCG 4275
 A   G   D   I   G   A   G   S   L   R   S   R   L   Q   T   Q   K   A   N   F   N   R   T   S
CATCCAAACCGGCCTTACTTTGGGCAATACAAGTTGGGTGACGACAGTGTTAAAGTAAGTTCTATGGCAGTGAAAAC   4350
 I   Q   T   G   L   T   L   G   N   T   L   K   I   N   Q   F   E   I   V   P   S   A   G   I   R
TTACAGCCGCCTGTCATCTGCAGATTACAAGTTGCTTATCGGTTAAAGTCGGCAACCTTGTTATCTGCAGC         4425
 Y   S   R   L   S   S   A   D   Y   K   L   G   D   D   S   V   K   V   S   S   M   A   V   K   T
ACTAACGCGGCCGACTGATTTGCTAATTGGCAAAGGCGGGTGAATGTGGGCGGTAAATCCTTCGCCTATAAAGCAGATAATCAACA 4500
 L   T   A   G   L   D   F   A   Y   R   F   K   V   G   N   L   T   V   K   P   L   L   S   A   A
TTACTTTGCCAATTATGGCAAAGGCGGGGTGAATGTGGGCGGTAAATGTTACATTGTTACATTAAACGTAAATGGCAGTATTACAAAAGGAAA 4575
 Y   F   A   N   Y   G   K   G   G   V   N   V   G   G   K   S   F   A   Y   K   A   D   N   Q   Q
GCAATATTCAGCAGGCGTCGCCGTTACTGTACCGTGATTGTTACATAATTAAACGTAAATGGCAGTATTACAAAAGGAAA  4650
 Q   Y   S   A   G   V   A   L   L   Y   R   N   V   T   L   N   V   N   G   S   I   T   K   G   K
ACAATTGGAAAAACAAAAATCCGACAATTAAAATACAGATTCGTTTCTAAAATACCAAATTCATAGCAAATA        4725
 Q   L   E   K   Q   K   S   G   Q   I   K   I   Q   I   R   F
AAATGCCGTCTGAACTCAAGCTTCGGACGGCATTTTATCAGACTAACAAAGCTACAGCTCAATGCCTTTGAGTT      4800

TCGCCACGGTATTGATGTCTTTGTCGCCGACCCGACAGTTGACCAAAATCACTTGTCTTTACCCATTTTCG         4875

GGCGCGTTTATCGCCCGGACCAA                                                         4899
```

FIG. 2A

```
CGCTTCCGATGCGCAAAGTGCAAATAAATCAAATCATTATCCGTAACGGGCATTTCA
 A  S  D  A  Q  S  A  N  K  Y  H  T  I  K  I  N  H  L  S  G  N  G  H  F  H

TTATCTGACGGACTTGGCGCAGAAAAATCTTGGGGATAAAGTGCTTGTGAAGGAATCCGGCATTATCAGCT     2850
 Y  L  T  D  L  A  K  N  L  G  D  K  V  L  V  K  E  S  A  S  G  H  Y  Q  L  889

CCATGTTCAAAATAAAAACAGGCGAACCTAATCAGGAAGGGCTGGATCTCTTTGATGCATCATCCGTACAAGACCG
 H  V  Q  N  K  T  G  E  P  N  Q  E  G  L  D  L  F  D  A  S  S  V  Q  D  R

CTCCCGCCTTTTGTTTCCTTGGCAAATCATTACGTCGATTTAGGCGCATTGCGTTATACAATCAAAACAGAAAA    3000
 S  R  L  F  V  S  L  A  N  H  Y  V  D  L  G  A  L  R  Y  T  I  K  T  E  N    939

CGGTATTACCCGGTTGTACAATCCTTATGCGGGAACGGCCGCCCAGTCAAGCCGTCTCCTGCCGCAAAC
 G  I  T  R  L  Y  N  P  Y  A  G  N  G  R  P  V  K  P  A  P  S* P* A* A* N*
                                                            a↑
CACGGCTTCTCAAGCACAAAAGGCAAATCAAGCCGAAGAAGCCCTCCGCCAACAAGCAAATGCCAAGCCTCAAAATATCGTCGTCGC    3150
 T* A* S* Q  A  Q  K  A  T  Q* T  D  G  A  Q  I  A  K  P  Q  N  I  V  V  A    989

ACCGCCTAGCCCGCAGGCAAATCAAGCCGAAGAAGCCCTCCGCCAACAAGCCCTCCGCCAACAAGCGGAGCAAGTGAAGCGTCA
 P  P  S* P* Q* A* N* Q* A* E* E* A* L* R* Q* A  K  A  E  Q  V  K  R  Q
   b↑
GCAAGCAGCAGAAGCAGAAAAAGTTGCACGTGCTCAAAAAGACGAAGAGGCAAAACGCAGCCGAAATTGCTCG    3300
 Q  A  A  E  A  E  K  V  A  R  Q  K  D  E  E  A  K  R  K  A  A  E  I  A  R    1039
```

FIG. 2B

```
TCAGCAGGAAGAAGCACGAAAAGCTGCAGAGTTAGCCGCCAAAACAAAAGGCGAAGCAGAGCGTAAAGCCAGAGA    3450
 Q  Q  E  E  A  R  K  A  A  E  L  A  A  K  Q  K  A  E  E  R  K  A  R  E        1089

GTTGGCAAGACAAAAGCAGAAGAGGCAAGTCATCAAGCTAATGCCAAACCAAAACGTCGTAGACGTCGGGCTAT    3600
 L  A  R  Q  K  A  E  E  A  S  H  Q  A  N  A  K  P  K  R  R  R  R  A  I        1139

ATTACCTAGACCTCCTGCCCCAGTATTTCATTGGATGATTATGATGCAAAAGACAATAGTGAATCATCAATAGG
 L  P  R  P  P  A  P  V  F  S  L  D  D  Y  D  A  K  D  N  S  E  S  S  I  G
              c

TAATTTAGCTCGTGTAATACCTAGAATGGGAAGGGAGTTAATTAATGATTATGAAGAAATCCCCTTGGAGGAGTT    3750
 N  L  A  R  V  I  P  R  M  G  R  E  L  I  N  D  Y  E  E  I  P  L  E  E  L     1189

GGAAGATGAAGCGGAAGAAGAACGTCGCCAAGCAATTCCACTCCAAAAGTCGTAACCGTAGAGCTATATC
 E  D  E  A  E  E  E  R  R  Q  A  T  Q  F  H  S  K  S  R  N  R  R  A  I  S

ATCGGAACCATCATCTGATGAAGATGAAGATCATCTGAATCGGTTTCCACATCAGACAAACACCCTCAAGATAATACGGA    3750
 S  E  P  S  S  D  E  D  A  S  E  S  V  S  T  S  D  K  H  P  Q  D  N  T  E

ACTTCATGAAAAGTTGAGACGGGCGGGGTTTACAACCAAGAGCCGCGAACCAGCCGCGAACCCGCCGCCAAGC
 L  H  E  K  V  E  T  A  G  L  Q  P  R  A  A  Q  P  R  T  Q  A  A  A  Q  A

CGATGCAGTCAGCACCAATACTAACTCGGCTTTATCTGACGCAATGGCAAGCACGCAATCTATCTTGTTGGATAC    3900
 D  A  V  S  T  N  T  N  S  A  L  S  D  A  M  A  S  T  Q  S  I  L  L  D  T     1239
```

FIG. 2C

```
AGGTGCTTACTTAACACGGCACATTGCACAAAAATCACGGCGCTGATGCCGAAAAAAACAGTGTTTGGATGTCAAA     4050
 G  A  Y  L  T  R  H  I  A  Q  K  S  R  A  D  A  E  K  N  S  V  W  M  S  N       1289

CACCGGTTATGGCCGTGATTATGCTTCCGCACAATATCGCCGTTAGTTCGAAACGCACGCAAACACAAATCGG        4200
 T  G  Y  G  R  D  Y  A  S  A  Q  Y  R  R  F  S  S  K  R  T  Q  T  Q  I  G       1339

CATTGACCGCAGCTTGTCCGAAAATATGCAGATAGGCGGAGTATTGACTTACTCTGACAGTCAGCATACTTTTGA      4200
 I  D  R  S  L  S  E  N  M  Q  I  G  G  V  L  T  Y  S  D  S  Q  H  T  F  D

TCAGGCGGGGGCGGCAAAAATACTTTTGTGCAAGCCAACCTTTATGGTAAGTATTATTAAATGATGCTTGGTATGT
 Q  A  G  G  K  N  T  F  V  Q  A  N  L  Y  G  K  Y  Y  L  N  D  A  W  Y  V

GGCCGGGCGATATTGGTGCGGGCAGCTTGAGAAGCCGGTTACAAACGCAGCAAAAAGCAAACTTTAACCGAACAAG     4350
 A  G  D  I  G  A  G  S  L  R  S  R  L  Q  T  Q  Q  K  A  N  F  N  R  T  S       1389

CATCCAAACCGGCTTACTTTGGGCAATACGCTGAAAATCAATTCGAGATTGTCCCTAGTGCGGGTATCCG
 I  Q  T  G  L  T  L  G  N  T  L  K  I  N  Q  F  E  I  V  P  S  A  G  I  R

TTACAGCCGCCTGTCATCTGCAGATTACAAGTTGGGTGACGACAGTGTTAAAGTAAGTTCTATGGCAGTGAAAAC      4500
 Y  S  R  L  S  S  A  D  Y  K  L  G  D  D  S  V  K  V  S  S  M  A  V  K  T       1439

ACTAACGGCCGACTGGATTTGCTTATCGGTTTAAAGTCGGCAACCTTACCGTAAAACCCTGTTATCTGCAGC
 L  T  A  G  L  D  F  A  Y  R  F  K  V  G  N  L  T  V  K  P  L  L  S  A  A
```

FIG. 2D

```
                                                                                  4650
                                                                                  1489
·TTACTTTGCCAATTATGGCAAAGGCCGGCGGGTGAATGTGGGCGGTAAATCCTTCGCCTATAAAGCAGATAATCAACA
  Y  F  A  N  Y  G  K  G  G  V  N  V  G  G  K  S  F  A  Y  K  A  D  N  Q  Q

·GCAATATTCAGCAGGCGTCGCGTTACTGTACCGTAATGTTACATTAAACGTAAACGTATTACAAAAGGAAA
  Q  Y  S  A  G  V  A  L  L  Y  R  N  V  T  L  N  V  N  G  S  I  T  K  G  K

·ACAATTGGAAAAACAAAATCCGGACAAATTAAAATACAGATTCGTTTCTAAAATACCAAATTCATAGCAAAATA
  Q  L  E  K  Q  K  S  G  Q  I  K  I  Q  I  R  F  1505
                                                                          ↓ 4800

·AAATGCCGTCTGAACTCAAGCTTCGGACGGCATTTTTATCAGACTAACAAAGCTACAGCTCAATGCCTTTGAGTT
                              ─────────────────────────→

·TCGCCACGGTATTGATGTCTTTGTCGCCGACCCGACAGGTTGACCAAAATCACTTGGTCTCTTTACCCATTTTCG

·GGCGGCGTTTTATCGCCCGGACCAA  4899
```

IgA1    Thr-Pro-Ser-Pro-Ser-Thr-Pro-Pro-Thr-Pro-Ser-Pro

IgA— (a):  Gly-Arg-Pro-Val-Lys-Pro-Ala-Pro-Ser-Pro-Ala-Ala-
           Asn-Thr-Ala-Ser-Gln-Ala-Gln-Lys-Ala

IgA— (b):  Glu-Asn-Ile-Val-Val-Ala-Pro-Ser-Pro-Glu-Ala-
           Asn-Gln-Ala-Glu-Gln-Ala-Leu-Arg-Gln

IgA— (c):  Glu-Glu-Leu-Pro-Arg-Pro-Pro-Ala-Pro-Val-Phe-
           Ser-Leu-Asp-Asp-Tyr-Asp-Ala-Lys-Asp

FIG. 7A

```
                                                              1079-1102
MS11:      CACGATAACGCCCGGCACCGTCAAA
(type 2)    H   D   N   A   G   T   V   K R16:       ------------------------
(type 2)

514:       -G----------------------
(type 2)    R

74:        -G---------------A------
(type 1)    R                I
```

FIG. 7B

```
MS11: TGGAAAACCACG---GGTACAAACAGCCATATCGGTTCGACAGCGGTAAGGCTTGCCAACAAT
       W  K  T  T  -  G  T  N  S  H  I  G  S  T  A  V  R  L  A  N  N

R16:  ----------------------------------------------------------------

514:  ------C-TT--TTCT--C--------A-G--T--C--T------------------GG-----
                N  I        S                  N                 G

74:   ------C-TT--TTCT--C--------A-G--T--C--T------------------GG-----
                N  I        S                  N                 G

GAAGGAGATGCGAACAACGGACAAAATGTTACCTTTGAAGACAACGGCACTTTGGTATTGAATCAA    1120-
 E  G  D  A  N  N  G  Q  N  V  T  F  E  D  N  G  T  L  V  L  N  Q     1246

```
MS11: AGGGTCGGCGACGGTACGGTTATTCTGAATCAAAAGCCGATGCCGACAAAAAGTTCAGGCTTTCTCCCAA    1459-
       K  V  G  D  G  T  V  I  L  N  Q  K  A  D  A  D  K  K  V  Q  A  F  S  Q   1603

R16:  ----------------------------TCA-----GC-GAT-CAAAC-G-----------------------
                                  I  K     P  I  Q  T  E

514:  ---A--------------------------C--GC-GATGC-GACA------GTCC-----------------
                                     H     P  M  P  T           S

74:   ---A--------------------------C--GC-GATGC-GACA------GTCC-----------------
                                     H     P  M  P  T           S

GTCGGGCATTGTCTCAGGCGGACGAGGTACACATTGGTATTAAATAGTTCAAATCAGATTAATCCCGATAATCTATAT
       V  G  I  V  S  G  R  G  T  L  V  L  N  S  S  N  Q  I  N  P  D  N  L  Y

```
MS11: GACCACGGCCTCCACAATCACACTAACGGGTAAATCTTTAATTACCAATCCGAACAGCCTTTCGGTA
       D  H  A  S  T  I  T  L  T  G  K  S  L  I  T  N  P  N  S  L  S  V

R16:  ------------------------------------------------------------------

514:  ------------------------------------------------------------------

74:   ------G-----------------------------------------T-----------------
            R
                                                                         1706-1831
      CATAGCATACAAAATGACTATGATGATGAAGATGATTATAGTTATTATTACCGACCAAGGCGA
       H  S  I  Q  N  D  Y  D  E  D  D  Y  S  Y  Y  Y  Y  R  P  R  R

```
MS11: AGGCTGAACGCACCGATGCCCGAGAACGGTGTAGCAGAAAATAACGACTGGATCTTT
       R  L  N  A  P  M  P  E  N  G  V  A  E  N  N  D  W  I  F

R16:  ---TG-T-----------------A-------ACA-A-G-----------T--A
       S        V                    Q   T                 L

514:  ---TG-T-----------------A-------ACA-A-G-----------T--A
       S        V                    Q   T                 L

74:   ---TG-T-----------------A-------ACA-A-G-----------T--A
       S        V                    Q   T                 L
```

1898-2011

```
      ATGGGATATACGCAGGAGGAGGCCAGGAAAAACGCGATGAACCACAAAAACAATCGG
       M  G  Y  T  Q  E  E  A  R  K  N  A  M  N  H  K  N  N  R

-----CAGC------------------------------------------------
           S

-----CAGC------------------------------------------------
           S

-----CAGC------------------------------------------------
           S
```

FIG. 7F

```
MS11: GAAGAAAACGGAAAAGGACATAACGGGCGCATTAAACCTTAATTTCAATGGCAAAAGC    2042-
       E  E  N  G  K  G  H  N  G  A  L  N  L  N  F  N  G  K  S     2098

```
MS11: GGGAACGGGCCGGCCCAGTCAAGCCGGCCCCGTCTCCTGCCGCAAAGACGGCTTCTCAAGCACAAAAGGCAACA
       G  N  G  R  P  V  K  P  A  P  S  P  A  A  N  T  A  S  Q  A  Q  K  A  T

R16:  -------------C---------------------------------------------------------
                  R

514:  -------------C-----------------------------C---------------------------
                  R

74:   -------------C-----------------------------C-G-------------------------
                  R                              G

CAAACGGACGGTGCACAAATTGCCAAGCCTCAAAATATCGTCGTGGCACCGCCTAGCCCGGCAGGCA   3032-3169
       Q  T  D  G  A  Q  I  A  K  P  Q  N  I  V  V  A  P  P  S  P  Q  A

----A-------G----T-----------------C--
                                              D
```

PROCESS FOR PRODUCING PROTEINS USING GRAM NEGATIVE HOST CELLS

DESCRIPTION

The invention concerns a process for the production of proteins using gram-negative host cells, into which a vector is introduced which contains at least one gene coding the desired protein, transcription of this gene and translation.

Gene-technological processes for the production of proteins have long been known. Preferably, microorganisms are used for this purpose which are easy to culture and which permit the extraction of the protein produced in a simple manner. A widely-used organism is E. coli which can very easily be cultured and the properties of which are very well known. It a disadvantage of this micro-organism species that, as a gram-negative micro-organism, they frequently does not discharge the proteins or polypeptides produced into the surroundings but, at most, gives them off into the periplasma. The working up is, therefore, laborious and can only take place with destruction of the microorganisms.

Admittedly, a plurality of proteins are secreted by gram-negative bacteria. It has been found, however, that, for the secretion, specific bacterial proteins are essential for the second translocation step through the structural genes membrane. The cloning of the corresponding structural genes led to the accumulation of these proteins in the periplasma of E. coli. The same effect is also described for the Haemophilus influenzas IgA-protease which is secreted extracellularly in the natural host but which, when it is cloned into E. coli, is found in the periplasm. Still more complex is the secretion of the E. coli haemolysine. Here, a total of 4 different protein components, which are coded on a single operon, are necessary.

It was, therefore, the object of the present invention to improve a process for the gene-technological production of proteins using gram-negative host cells so that the desired protein, after its formation in the host cell, is discharged from the cell and can then be obtained extracellularly from the culture medium.

This task was solved by a process for the gene-technological production of proteins with the use of gram-negative host cells in which a vector is introduced, which contains at least one gene coding the desired protein, transcription of this gene and translation, which is characterised in that for the extracellular obtaining of the protein, one inserts its coding gene into a vector which contains the IgA-protease precursor gene from micro-organisms of the species Neisseria, in such manner that the coding gene is positioned within the sequence of the IgA-protease precursor gene.

Various pathogenic types of bacteria of the species Neisseria, such as Neisseria gonorrheae and Neisseria meningitidis, which grow on the human raucous membrane, emit extracellular proteases, which are specific for hurian IgA 1. This immunoglobulin is, besides IgA 2, the main component of the secretory immunity which is to protect against infections by such pathogens. Related types of bacteria which are not pathogenic produce no IgA-proteases.

The IgA-protease gene obtained from Neisseria displays surprising properties. The IgA-protease formed or its precursor can be actively secreted not only in the natural host but also in foreign gramnegative host cells, such as Enterobacteriaceae. A single gene which codes a large precursor suffices for the production and extracellular secretion of IgA-protease even in foreign host cells. This precursor, which, with a molecular weight of 170 kd, is approximately 63 kd larger than the final extracellular IgA-protease, which only has a molecular weight of 106 kd.

The precursor protein is converted into the final extracellular IgA protease during transport through the membrane of the gram negative host cell. Processing leading to the final product includes autoproteolytic activity of the enzyme. This autoproteolytic activity involves splitting off of some parts of the precursor molecule leading to the final, active form of the IgA protease. This precursor protein is coded by a DNA fragment with 5 Kb.

The precursor has 3 functional domains, a homogeneous amino-terminal leader peptide, the actual protease component and a relatively large carboxy-terminal helper component.

The leader peptide guides the IgA-protease precursor into the periplasmic gap and is removed from the precursor via a signal peptidase of the inner membrane. The initial step in the transport of the IgA-protease could, therefore, be equated with a regular co- or post-translation path which is followed by the majority of the periplasma and outer membrane proteins.

In a second step, the remaining precursor complex, which consists of protease and helper component, is transported into the outer membrane and is released extracellularly. The mechanistic course of this process can be explained by the helper function of the IgA-protease-precursor complex. The amino-terminal helper component is strongly polar, whereas the carboxy-terminal component is rather hydrophobic and displays features which are typical of a membrane addition. One explanation arising from these observations is that the helper forms a pore in the outer membrane, and the hydrophilic portions of the remaining precursor molecule project into this pore. The actual protease component, which is still connected to the helper, is then thrust through this pore and assumes its active configuration extracellularly. A sequential autoproteolytic processing then discharges the final, active form of the IgA-protease into the extracellular surroundings. The energy which is necessary for the active transport originates from the autoproteolytic splitting off of the helper.

To obtain extracellular obtaining of a desired protein, its coding gene is inserted, in per se known manner, into a vector which contains the IgA-protease gene of Neisseria. The sequence of coding regions for this IgA-protease, gene consists, as stated above, of three main domains, i.e., the leader component, the sequence which codes for the IgA-protease itself and the helper component. Surprisingly, it has now been found that between the proteasecoding region and the helper domain or within the helper domain, there are three natural cleavage positions. These cleavage positions, which are designated in the gene sequence shown in FIG. 2A as "a" and "b", and in FIG. 2B or "C" are formed by the following amino acids:

cleavage position (a): Pro-Ala-Pro-Ser-Pro
cleavage position (b): Pro-Pro-Ser-Pro
cleavage position (c): Pro-Arg-Pro-Pro-Ala-Pro.

The coding sequence for the desired protein can now be inserted into different regions of the IgA-protease gene. An insertion into the leader component is not considered herein because this component is split off during the passage through the inner membrane.

One variant of the process according to the invention involves the insertion into the IgA-protease domain of the gene coding the desired protein. At certain points in the protease domain of the IgA-protease precursor gene, this insertion is possible without destruction of the IgA-protease activity. In this case, the IgA-protease precursor is expressed, whereby the desired protein is found within the protease component.

The still inactive IgA-protease or its precursor is expressed in the above-described manner. The desired protein is then present connected to the protease which is still at least partly active. The separation from the protease then takes place either by processing of the protease, by a protease suitable therefor or by chemical reactions.

The gene coding for the desired protein can also be inserted in the IgA-protease domain so that no more active IgA-protease can be formed and thus IgA-protease activity is no longer present. In this case, a preferred form of the process according to the invention involves introducing a vector which carries the whole IgA-protease gene either into the same bacterium or into another bacterium which is cultured simultaneously. The IgA-protease which is then formed simultaneously with the desired protein can separate the desired protein from the helper and thus from the membrane wall and thus make possible the obtaining from the culture medium.

In a preferred embodimental form of the process according to the invention, the gene sequence which codes the desired protein is inserted in a gene section of the IgA-protease precursor gene which lies between the natural cleavage sites (a), (b) and/or (c). In this case, one obtained active IgA protease the protease with attached, desired protein, passes through the two membranes of the host cell, as the precursor is naturally cleaved via the steps detailed supra. The desired protein is then separated from the protease and is present in free form in the culture medium, from which it is then obtained.

The incorporation of the protein gene into the protease domain of the IgA gene can also be so carried out that parts or the entire IgA-protease domain are destroyed. Even with destruction of IgA protease activity, nontheless the desired protein is expressed and is discharged through the two membranes of the gram-negative bacterial host cell. Since protease activity is lacking, and it is protease activity which separates the helper associated with the membrane from the enzyme, the protein remains bound to the helper and is thus associated with the cell wall. This embodiment of the invention is especially suitable for the production of living vaccines. In this was, for example, a surface antigen can be bound to the outer membrane of the gram-negative micro-organism and used for the production of antibodies.

For the production according to the invention of the desired protein, gram-negative host cells, especially micro-organisms of the family Enterobacteriaceae, are very well suited. Preferably, micro-organisms of the genus Escherichia and Salmonella are used. A study of the strains E. coli, Salmonella typhimurium and of weakened Salmonella typhii has shown that with these host cells even higher activities of IgA-protease are given off into the supernatant than in the case of N. gonorrhoeae, the natural host. The secretion of the IgA-protease in all these gram-negative systems is based upon the same mechanism because the extracellular enzymes are identical and are processed from the same precursor.

The process according to the invention is suitable for the obtaining of proteins. Especially preferred is a process in which biologically or therapeutically active proteins are obtained. A further use of the process according to the invention involves the expression of antigenic epitopes for use in gram-negative bacterial live vaccines.

The process according to the invention is especially preferably carried out with E. coli DSM 3775 as host cell, which contains the plasmid pIP 100. This plasmid pIP 100 is derived from the plasmid pBR 322 and carries the entire gene sequence of the IgA-protease precursor.

The process according to the invention makes it possible to obtain proteins in a simple manner. The proteins can be obtained from the culture medium, although gram-negative bacteria are used as host cells which are easy to culture.

The DNA fragment used according to the invention coding for the IgA-protease precursor has a total sequence of 4899 base pairs which form a single interconnected open reading frame with a length of 4602 base pairs. The gene sequence is to be seen in FIGS. 1A, 1B, 1C and 1D.

The ATG start codon, which is the third codon of the open reading frame, and a sequence which is similar to the Shine-Dalgarno consensus sequence, shows a translation initiation site at position 104. The translation ends with a TAA ochre stop codon at position 4700. An AT-rich region in front of the translation initiation signal shows the typical features of a promotor and directs the transcription of the IgA-protease gene. A palindrome sequence, which follows the translation stop codon, can serve as transcription terminator.

A precise evaluation of the nucleotide sequence data gave a totality of 1532 amino acids for the IgA-protease precursor, which gives a protein with 169 kd The complete precursor sequence contains only two cysteine residues, which were found at a spacing of 11 amino acids. This is interesting because the absence of cysteine is characteristic of many secretory proteins. The hydrophilic profile gives a very regularly alternating pattern with some outstanding features: a short hydrophobic segment on the amino-terminal end forms a typical secretory signal peptide which shows 4 positive amino-terminal charges and a central hydrophobic region. The cleavage site of this segment, designated as leader peptide, is located between 2 alanine radicals in the positions −1 and +1 (FIG. 1A). The most conspicuous features of the primary structure of the precursor are, however, two outstanding hydrophilic regions to the right of the central region of the precursor and a short one on its carboxy end.

The part which corresponds to the completed extracellular IgA-protease is located subsequent to the leader peptide in the amino-terminal region of the precursor molecule.

The boundary region between protease and helper contains various proline-rich regions which show striking sequence agreements with the cleavage site of the IgA-protease from N. gonorrhoeae in the case of human IgA 1. FIG. 2A shows amino acid sequences of two of these sites, marked "a" and "b", and FIG. 2B shows the third, marked "c". These sites are the autoproteolytic attacking sites for the IgA-protease. In order to confirm this, the cleavage was examined with the enzyme in trans. For this purpose, MS2/IgA-protease fusion proteins were isolated in preparative amounts on gel and incubated with small quantities of purified IgA-protease. The incubation of different IgA-protease fusion with active enzyme indeed led to specific decomposition products. The fusion protein fp 180 shown in FIG. 3B was split into two main products with 120 and 60 kd and two smaller products of 45 and 15 kd. Control incubations are negative as is to be expected for a specific reaction with IgA-protease. When using a monoclonal antibody which is directed against the final protease, the 120 kd band reacts in the immunoblot. Antiserum which is directed against the fp 42 fusion protein (FIG. 3B) gives a cross-reaction with the 60 kd and 45 kd products and also with the 15 kd product. The cross-reaction with the 120 kd product is based upon the MS2 polymerase component in the fusion proteins. These data confirm that the sites (a) and/or (b) are indeed the attacking sites of the IgA-protease. The 45 kd and the 15 kd products probably result by partial digestion at the site (c) (FIG. 2B). Besides these positions, apparently no other regions in the fusion proteins are accepted as attacking sites by the IgA-protease.

More detailed information regarding the internal precursor attack sites was obtained by an amino-terminal sequence analysis of the 60 kd cleavage product (FIG. 3D). This protein fragment appeared as a diffuse band in the acrylamide gel and, according to the gene map, it represents the carboxy-terminal portion of the precursor (FIG. 1D). The analysis gave unambiguous data for the sequencing steps 1, 2, 4, 5, 7 and 9 to 13. For all the other steps up to position 8, the sequence analysis gave signals from two amino acids. One of these two amino acids respectively at each position coincided with the sequence at the site (a) or at site (b) (FIG. 2A). The positions 9 to 13 coincide with the amino-terminal sequence of site (b). Therefore, the heterogeneity of the protein sequence confirms the use of two sites (a) and (b) as attacking sites for the IgA-protease.

The observation that the finished IgA-protease, which was prepared from culture supernatants of *N. gonorrhoeae*, is a heterogeneous protein which forms a 106/109 kd double band in acrylamide gel can be explained by heterogeneous carboxy termini of the final IgA-protease corresponding either to site (a) or to site (b). The 3 kd peptide segment which bridges the distance between the positions (a) and (b) might be responsible for the difference in the molecular weights of the two forms.

In the crude supernatants, an additional band of 121 kd can be shown which also belongs to the IgA-protease. This band cross-reacts not only with anti-protease serum but also with antiserum against the fusion protein fp 42 which demonstrates that the 121 kd protein carries a demarcated portion of the helper. In accordance with its size, the carboxy end of the intermediate product is located exactly at position (c) (FIG. 2C), one of the internal attack sites of the IgA-protease precursor.

The relative amounts of the 3 forms of the extracellular IgA-protease were determined in a growing *E. coli* culture. The results of this experiment show that, in the early growth phase, the 121 kd intermediate product predominates. When the enzyme accumulates during the period of growth, the 109 kd intermediate product predominates and finally the final 106 kd form of the IgA-protease can be clearly demonstrated. This points to the slow transformation of the high molecular weight intermediate product into the final enzyme. This agrees with the observation that the intermediate product with 109 kd molecular weight, which is still contained as main fraction in some IgA-protease preparations, is slowly converted into the low molecular weight form after comparatively long storage.

These experiments show that at least the polar portion of the helper is extracellularly secreted together with the IgA-protease itself. By immunoblotting it could be shown that the small 12 kd part of the helper, which is present between the internal cleavage sites (b) and (c), is indeed released into the extracellular surroundings together with the IgA-protease. It is concluded that the polar properties of this region are especially important for the extra-cellular secretion of the IgA-protease.

It is assumed that the pathogenity of the microorganisms of the genus Neisseriea is possibly to be attributed to the formation of the IgA-protease. Therefore, a possible means for combatting the serious illnesses caused by these micro-organisms involves blocking the cleavage sites of the IgA-protease precursor so that the precursor can no longer be cleaved, i.e. its own cleavage sites are no longer recognised and thus the active enzyme which is held responsible for the harmful effects of the microorganism, cannot be formed.

In order to block of the cleavage sites of the precursor molecule, substances are preferably used which are capable of binding with the amino acid sequences forming the cleavage sites (a), (b) and/or (c), especially antibodies directed against these amino acid sequences.

A further possible approach is to block the cleavage sites of the IgA-protease by adding peptide analogues which have a slightly modified amino acid sequence with respect to the sequence of the cleavage site these accumulate on the cleavage sites but cannot be cleaved and thus remain adhering to the interface.

The invention is explained by the following Examples in conjunction with the Figures.

BRIEF DESCRIPTION OF THE FIGURES

FIG. 1A presents a portion of the DNA sequence coding for the IgA protease precursor gene of the invention, and the amino acid sequence for which it codes.

FIG. 1B continues the presentation of the IgA protease precursor coding sequence which begins in FIG. 1A.

FIG. 1C continues the coding sequence.

FIG. 1D continues, and completes the coding sequence.

FIG. 2A shows analysis of the coding sequence for the IgA protease of *N. gonorrheoeae* strain MS11.

FIG. 2B continues the analysis of the sequence.

FIG. 2C continues the analysis further.

FIG. 2D continues and concludes the analysis.

FIG. 7A shows a portion of the gene and amino acid sequence of IgA protease from differing gonococcal strains.

FIG. 7B compares different regions of these strains.
FIG. 7C compares different regions of these strains.
FIG. 7D presents further comparisons.
FIG. 7E compares additional sequences.
FIG. 7F continues the comparison.
FIG. 7G concludes the comparison.

Example 1

Figure 3A:
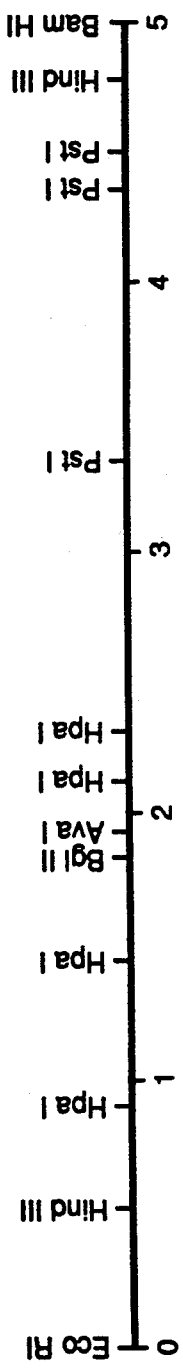
FIG. 3A is a restriction map of pIp 100, which contains the IgA protease precursor gene.
Figure 3B:
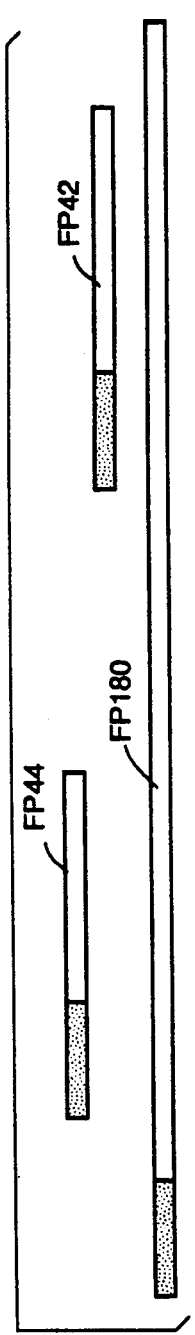
FIG. 3B shows, schematically, the fusion proteins of IgA protease, produced in the pEX expression system.
Figure 3C:
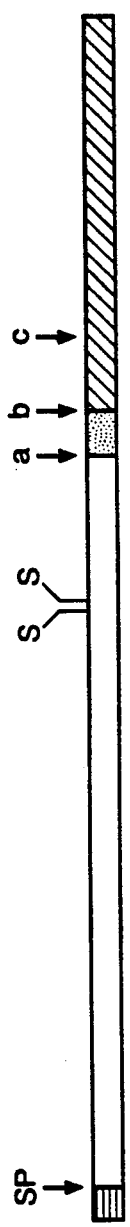
FIG. 3C presents, schematically, the IgA protease precursor, showing signal peptide and internal IgA protease cleavage sites.
Figure 3D:
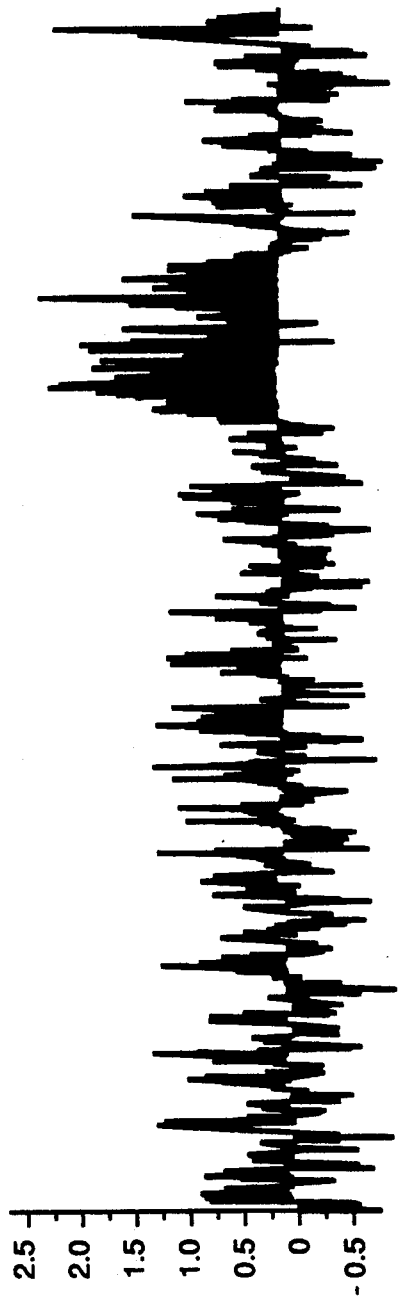
FIG. 3D displays hydropathy blots of the amino acid sequence for IgA protease precursor.
Figure 4:
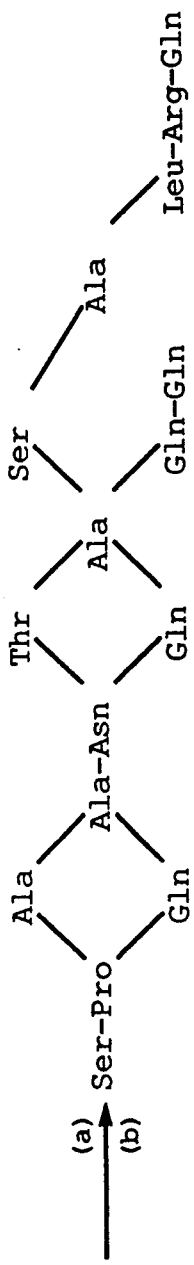
FIG. 4 presents the cleavage sites for IgA protease, as well as an amino acid sequence analysis.
Figure 5:
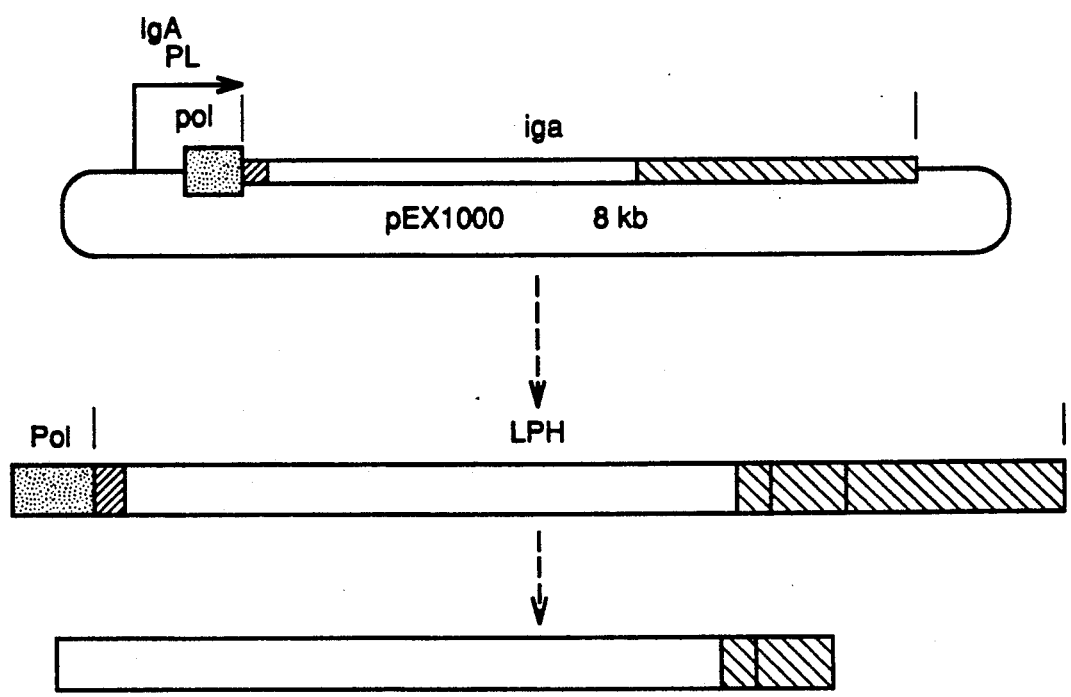
FIG. 5 outlines the production of a vector which overproduces IgA protease.
Figure 6:
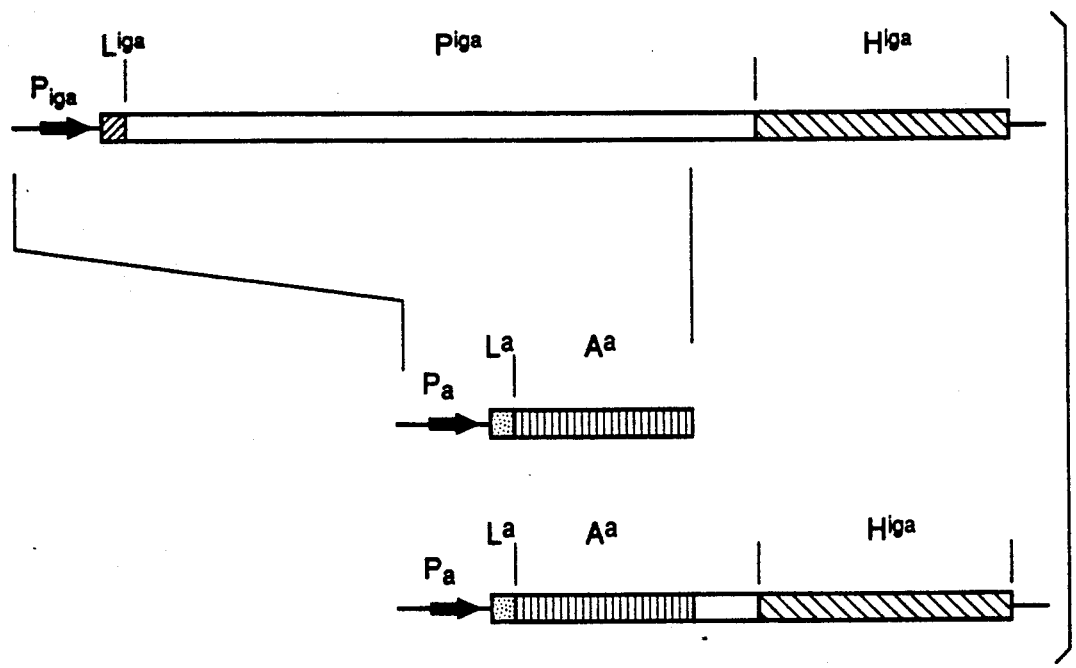
FIG. 6 outlines how the original IgA protease promoter (piga) was exchanged with promoter "Pa" from antigen A.

Overproduction of IgA-protease and optimization of the transport into the culture supernatant With the help of synthetic oligonucleotides, the complete gene of the IgA-protease precursor was fused with the MS2-polymerase gene in the pEX expression system (see FIG. 5). The resulting plasmid pEX 1000 leads, in the cytoplasm of the host cell, to the expression of a large hybrid protein consisting of the amino-terminal 99 amino acids of the MS2-polymerase, bound with the total amino acid sequence of tile IgA-protease precursor. In the course of the secretion, this fusion protein is cleaved proteolytically and results in the liberation of the IgA-protease, as well as of the intermediate, into the culture supernatant. By deletion of less amino acids in the secreted segment of the helper, not only the efficiency but also the quality of the IgA-protease secretion was considerably increased (see Table 1).

Table 1 compares the IgA-protease secretion of various kinds of bacteria, as well as the effects of changes of the expression signals, as well as of modifications in the gene of the IgA-protease. The amount of protein was determined in SDS-polyacrylamide gels and Western blot analyses.

TABLE 1

| | introduced amino acids | removed amino acids | effectiveness of the secretion |
|---|---|---|---|
| N. gonorrhoeae MS 11 | | | 0.05 mg./l. |
| pIP 100 (E. coli) | — | — | 0.05 |
| pIP 100 (S. typhi, Ty21a) | — | — | 2.0 |
| pEX 1000 | — | — | 0.5 |
| pEX 1000 A51 | Arg—Asn—Ser—Gly$^{(772)}$ | — | 0.5 |
| pEX 1000.R9 | Ser—Gly—Ile—Pro$^{(945)}$ | — | 0.5 |
| pEX 1000.A36 | Ala—Gly—Ile—Pro$^{(1077)}$ | — | 0.2 |
| pEX 1090 | — | 1080,1081 | 0.5 |
| pEX 1080 | — | 1080–1083 | 0.7 |
| pEX 1070 | — | 1080–1084 | 2.0 |
| pEX 1072 | — | 1065–1084 | 2.0 |
| pEX 1073 | — | 1048–1084 | 2.0 |

EXAMPLE 2

Incorporation of oligopeptides into the IgA-protease precursor and transport into the culture supernatant With the use of gene-technological methods, into the gene of the IgA-protease a synthetic DNA double strand 12 bp long was incorporated at three positions. After translation of the protein, this corresponded to an insertion of four additional amino acids, respectively. All three insertions (see Table 1) show no influence on the transport and the enzymatic activity of the IgA-protease. For the plasmids pEX 1000. A51, —.R9 and —.A36 (see FIG. 5 and Table 1), it was shown in SDS-polyacrylamide gels and with the immunoblot technique that in the supernatant of the bacteria the same intermediates and the same end state of the IgA-protease occur as in the original clone pIP 100. The inserted oligopeptide in pEX 1000.A36 is located between the cleavage sites (b) and (c) and is thus given off, after autoproteolysis, in conjunction with the 12 kd cleavage product, solubly into the medium.

EXAMPLE 3

Substitution of expression signal and of the protease domain

The carboxy-terminal 60 kd sized helper domain of the IgA-protease precursor protein is necessary 17or the transport of the protease domain over the outer membrane. In order to strengthen the fundamental importance of the helper in the case of the protein secretion, large parts of the protease domain $P^{iga}$, the promotor $P_{iga}$ and the signal sequence $L^{iga}$ were substituted with gene technological methods. The exchange took place against a fragment which, for its part, contained the signals for (i) gene expression, $P_a$ for (ii) the protein transport over the inner bacterial membrane, the signal sequence $L^a$. Furthermore, the fragment provided a sequence (iii) which coded for the antigen $A^a$. Translational fusions with the helper sequence $H^{iga}$ permitted a helper-specific protein band of about 36 kd to be detected in culture supernatants of recombinant E. coli cells. For this purpose, a monoclonal antibody was used. Hitherto, it had not been possible to detect a complete fusion protein of the expected size. However, the detection of the 45 kd helper-specific protein in the whole cell lysates of recombinant clones was successful but not in their culture supernatants. From this observation, it is concluded that the 36 kd sized helper-specific protein is a degradation product of the 45 kd helper band. The described degradation was hitherto only observed in recombinant E. coli cells but not in the natural host.

We claim:

1. Method for producing a protein, comprising:
   (i) transforming a gram negative host cell with a vector which contains a DNA sequence coding for a fusion protein, said fusion protein comprising:
      (a) an N-terminal leader segment which is capable of directing said fusion protein through an inner membrane of gram negative bacteria;
      (b) a C-terminal portion comprising a 60 kd Neisseria IgA protease precursor protein helper segment;
      (c) a protein which is heterologous to said host cell and the source of said Neisseria IgA protease precursor protein,
   (ii) culturing said gram negative host cell under conditions favoring production of said fusion protein, and,
   (iii) obtaining secreted polypeptide which comprises said foreign protein portion.

2. The method of claim 1, further comprising introducing a vector which codes for an active Neisseria IgA protease into a second host cell and simultaneously culturing said second host cell and said gram negative host cell under conditions favoring production and secretion of said active Neisseria IgA protease and said secreted polypeptide, and cleavage of said secreted polypeptide in an extracellular environment by said active Neisseria IgA protease.

3. The method of claim 1, wherein said gram negative host cell is an Enterobacterium.

4. Method of claim 1, wherein said gram negative host cell is an *Escherichia coli* host cell.

5. Method of claim 1, wherein said Neisseria is *Neisseria gonorrhoeae*.

6. Method of claim 1, wherein said DNA sequence consists of:
   (i) a 5'-sequence coding for a Neisseria IgA leader segment,
   (ii) a sequence coding for the IgA protease segment of a Neisseria IgA protease precursor segment,
   (iii) a sequence coding for a Neisseria IgA helper segment, and
   (iv) a 3'-sequence coding for said foreign protein positioned within said sequence, with the proviso that said foreign protein coding sequence is positioned such that it does not destroy the function of said C-terminal helper segment.

7. The method of claim 6, wherein said sequence coding for a foreign protein is positioned in said Neisseria DNA sequence at a position within a boundary region between said IgA protease segment and said IgA helper segment defined by two natural cleavage sites of Neisseria IgA protease precursor protein.

8. The method of claim 7, wherein said natural cleavage sites are located after amino acid 959, amino acid 991, or amino acid 1094 of FIG. 2.

9. An isolated DNA sequence which codes for an IgA protease precursor helper segment corresponding to amino acids 1095-1505 of FIG. 2.

* * * * *

UNITED STATES PATENT AND TRADEMARK OFFICE
CERTIFICATE OF CORRECTION

PATENT NO. : 5,268,270
DATED : December 7, 1993
INVENTOR(S) : Thomas F. Meyer, et al.

It is certified that error appears in the above-indentified patent and that said Letters Patent is hereby corrected as shown below:

Column 8, line 9,

-- 1. A method for producing a protein, comprising:

(i) transforming a gram negative host cell with a vector which contains a DNA sequence coding for a fusion protein, said fusion protein comprising:

(a) an N-terminal signal sequence which is capable of directing said fusion protein through an inner membrane of gram negative bacteria;

(b) a protein which is heterologous to said host cell and the source of said Neisseria IgA protease precursor protein;

(c) a C-terminal portion comprising a 60 kd Neisseria IgA protease precursor protein, (ii) culturing said gram negative host cell under conditions favoring production of said fusion protein, and (iii) isolating heterologous protein from said fusion protein. --.

Column 9, line 1,
Claim 4, change "Method" to -- The method --.

Column 9, line 1,
Claim 5, change "Method" to -- The method --.

UNITED STATES PATENT AND TRADEMARK OFFICE
CERTIFICATE OF CORRECTION

PATENT NO. : 5,268,270
DATED : December 7, 1993
INVENTOR(S) : Thomas F. Meyer, et al.

It is certified that error appears in the above-indentified patent and that said Letters Patent is hereby corrected as shown below:

-- Column 9, line 4.

-- 6. The method of claim 1, wherein said DNA sequence consists of:

(i) a 5'-sequence coding for a Neisseria IgA signal sequence, (ii) a sequence coding for the IgA protease segment of the Neisseria IgA protease precursor segment, (iii) a sequence coding for the Neisseria IgA helper segment, and (iv) a sequence coding for a heterologous protein, wherein said sequence coding for the heterologous protein is inserted in said sequence coding for the IgA protease precursor, with the proviso that it is positioned such that it does not destroy the function of said C-terminal IgA helper sequence. --.

Signed and Sealed this

Sixth Day of September, 1994

Attest:

BRUCE LEHMAN

Attesting Officer     Commissioner of Patents and Trademarks